(12) United States Patent
Nakamura et al.

(10) Patent No.: US 8,048,073 B2
(45) Date of Patent: Nov. 1, 2011

(54) ENDOSCOPIC INSTRUMENT WITH STEPWISE ADJUSTMENT OF PROJECTION LENGTH

(75) Inventors: Tsutomu Nakamura, Tokyo (JP); Keita Suzuki, Tokyo (JP); Yuta Muyari, Tokyo (JP); Shunsuke Motosugi, Hirosaki (JP)

(73) Assignee: Olympus Medical Systems Corp., Tokyo (JP)

( * ) Notice: Subject to any disclaimer, the term of this patent is extended or adjusted under 35 U.S.C. 154(b) by 840 days.

(21) Appl. No.: 12/115,038

(22) Filed: May 5, 2008

(65) Prior Publication Data

US 2008/0281153 A1 Nov. 13, 2008

(30) Foreign Application Priority Data

May 7, 2007 (JP) .............................. P2007-122524

(51) Int. Cl.
*A61B 18/14* (2006.01)
(52) U.S. Cl. .......................................... 606/46; 606/41
(58) Field of Classification Search ................... 606/41, 606/46, 48–50
See application file for complete search history.

(56) References Cited

U.S. PATENT DOCUMENTS

| | | | |
|---|---|---|---|
| 5,843,091 | A | 12/1998 | Holsinger et al. |
| 6,626,603 | B2 | 9/2003 | Gudaitis et al. |
| 2002/0095146 | A1 | 7/2002 | Hutchins et al. |

FOREIGN PATENT DOCUMENTS

| | | |
|---|---|---|
| JP | S61-191012 | 11/1986 |
| JP | H3-102785 | 10/1991 |
| JP | 2004-544 | 1/2004 |

OTHER PUBLICATIONS

Korean Notice of Allowance dated Jul. 27, 2010 together with an English language translation.

*Primary Examiner* — Michael Peffley
*Assistant Examiner* — Daniel Fowler
(74) *Attorney, Agent, or Firm* — Scully, Scott, Murphy & Presser, P.C.

(57) ABSTRACT

An endoscopic instrument includes: a knife; a wire having a distal end connected to the knife; a sheath around the wire; a main body having the freely rotative sheath fixed thereto; a slider fixed to the wire, slidable in an axial direction of the main body; a stopper projecting radially from the wire; a first-distal-regulation section in the sheath for regulating distal sliding movement of the wire by making contact with the stopper; and a second-distal-regulation section, provided distal to the first-distal-regulation section, for regulating sliding movement of the wire by making contact with the stopper, wherein the stopper is capable of moving between the first-distal-regulation section and the second-distal-regulation section by rotating the main body relative to the sheath around an axial line by predetermined angle, and at least two different projection lengths can be maintained by contacting the main body to the first-distal-regulation section or the second-distal-regulation section.

6 Claims, 8 Drawing Sheets

FIG. 12

ENDOSCOPIC INSTRUMENT WITH STEPWISE ADJUSTMENT OF PROJECTION LENGTH

BACKGROUND OF THE INVENTION

1. Field of the Invention

The present invention relates to an endoscopic instrument inserted into an operation channel of an endoscopic apparatus.

The present application claims priority to Japanese Patent Application No. 2007-122524 filed May 7, 2007, the content of which is incorporated herein by reference.

2. Background Art

Conventionally known instruments, e.g., needle knives for endoscopic insertion use into body cavity incise mucosa etc. using high-frequency electric current (see Japanese Unexamined Utility Model (Registration) Application Publication No. S61-191012, hereinafter called Patent Document 1). Instruments of this type have an incising section, e.g., an interventional needle knife on a distal end of a wire inserted into an insulative sheath inserted through all endoscope channel. The incising section is capable of freely projecting or retracting relative to the distal end of the sheath by maneuvering a maneuvering member having a proximal end of the wire attached thereon.

Projection length, which is generally short, of the incising section of the aforementioned instrument cannot be adjusted easily. Also, in many cases, the maneuvering amount of the maneuvering member does not correspond to the projecting/retracting amount of a distal end member equally since the endoscope inserted into a body cavity makes complex curves. This enables only two-step adjustment of the incising section, i.e., full projection state and full retracted state into a sheath under present circumstances.

An endoscopic incision instrument proposed for solving the problem has an engagement section having a greater diameter than an inner diameter of a sheath disposed on an electrode or a maneuvering section located in the sheath. This enables fine adjustment of the projection length by means of preload applied when extending or retracting the incising section (see Japanese Unexamined Patent Application, First Publication No. 2004-544, hereinafter called Patent Document 2).

However, adjusting the projection length of the incising section by the incision instrument proposed in Patent Document 2 necessitates observing an image of the distal end picked up by the endoscope distally slantwise. The above method is difficult to reliably obtain desirable projection length since generally the projection length is subject to small pitch, e.g., 0.5 mm etc.

The present invention was conceived in consideration of the aforementioned circumstances, and an object thereof is to provide an endoscopic instrument that can easily and reliably adjust and maintain two or more stepwise projection length of the incising section relative to a sheath.

SUMMARY OF THE INVENTION

The present invention is an endoscopic instrument which includes: an incising section inserted into a body cavity endoscopically for incisional intervention; a wire having a distal end connected to the incising section; a sheath, made from insulative material, for allowing the wire to pass therethrough; a main body having a proximal end of the sheath fixed thereto, the proximal end being capable of freely rotating in a circumferential direction; a slider, having a proximal end of the wire fixed thereto, disposed slidably in an axial line direction of the main body; a stopper, provided to the incising section or the wire, for projecting outward radially relative to the wire; a first-distal-regulation section, provided to the sheath, for regulating distal sliding movement of the wire by making contact with the stopper; and a second-distal-regulation section, provided distally relative to the first-distal-regulation section, for regulating distal sliding movement of the wire by making contact with the stopper, wherein the stopper is capable of moving between the first-distal-regulation section and the second-distal-regulation section by rotating the main body relative to the sheath around an axial line by a predetermined rotational angle, and the incising section can be maintained at two different projection lengths based on the stopper making contact with the first-distal-regulation section or the stopper making contact with the second-distal-regulation section distal-regulation section.

Note that, in the present invention, "proximally" or "proximal end" indicates where a slider, which will be explained later, is disposed with respect to sliding direction of the wire; and "distally" or "distal end" indicates where the incising section is disposed.

The endoscopic instrument according to the present invention rotating the main body relative to the sheath and causing the stopper to make contact with one of the first-distal-regulation section and the second-distal-regulation section maintains at least two different stepwise projection lengths of the incising section projecting from the sheath.

The stopper may be capable of moving between the first-distal-regulation section and the second-distal-regulation section by engaging mating engagement sections provided to the stopper and to the first-distal-regulation section and by rotating the main body relative to the sheath around the axial line by the predetermined rotational angle.

The first-distal-regulation section and the second-distal-regulation section may be engagement grooves, formed on an inner periphery of the sheath, and the first-distal-regulation section and the second-distal-regulation section may be connected by cam grooves provided on the inner periphery of the sheath; the stopper having engagement projection sections engaging with the engagement grooves, and the stopper upon moving the engagement projection sections on the cam grooves may move between the first-distal-regulation section and the second-distal-regulation section.

The first-distal-regulation section and the second-distal-regulation section may be a first abutment surface and a second abutment surface provided proximally relative to a projection-length-adjusting member fixed to the sheath, and the first abutment surface and the second abutment surface may be disposed at different positions in circumferential directions with respect to the projection-length-adjusting member.

In addition, the present invention is an endoscopic instrument which includes: an incising section inserted into body cavity endoscopically for incisional intervention; a wire having a distal end connected to the incising section; a sheath, made from insulative material, for allowing the wire to pass therethrough; a main body having a proximal end of the sheath fixed thereto, the proximal end being capable of freely rotating in a circumferential direction; a slider, having a proximal end of the wire fixed thereto, disposed slidably in an axial line direction of the main body; a stopper, provided to the incising section or the wire, for projecting outward radially relative to the wire; and which screw engagement members, inserted and in a distal end of a sheath and fixed thereinside, for regulating distal sliding movement of the wire, wherein a screw groove is formed on one of the stopper and the screw engagement members, and a screw thread engaging with the screw groove is formed to the other, and the projection length of the incising section can be adjusted steplessly by changing both the screw engagement length of the stopper and the screw engagement members.

The wire may be a multi-thread coil or a multi-thread-and-multi-layer coil.

The endoscopic instrument according to the present invention can easily and reliably adjust and maintain two or more stepwise projection length of the incising section relative to a sheath. Therefore, intervention corresponding to the shape of object tissue can be conducted by desirably adjusting the projection length of the knife 2.

PREFERRED EMBODIMENTS

An endoscopic instrument (simply hereinafter called an instrument) according to a first embodiment of the present invention will be explained with reference to FIGS. 1 to 6.

Figure 1:
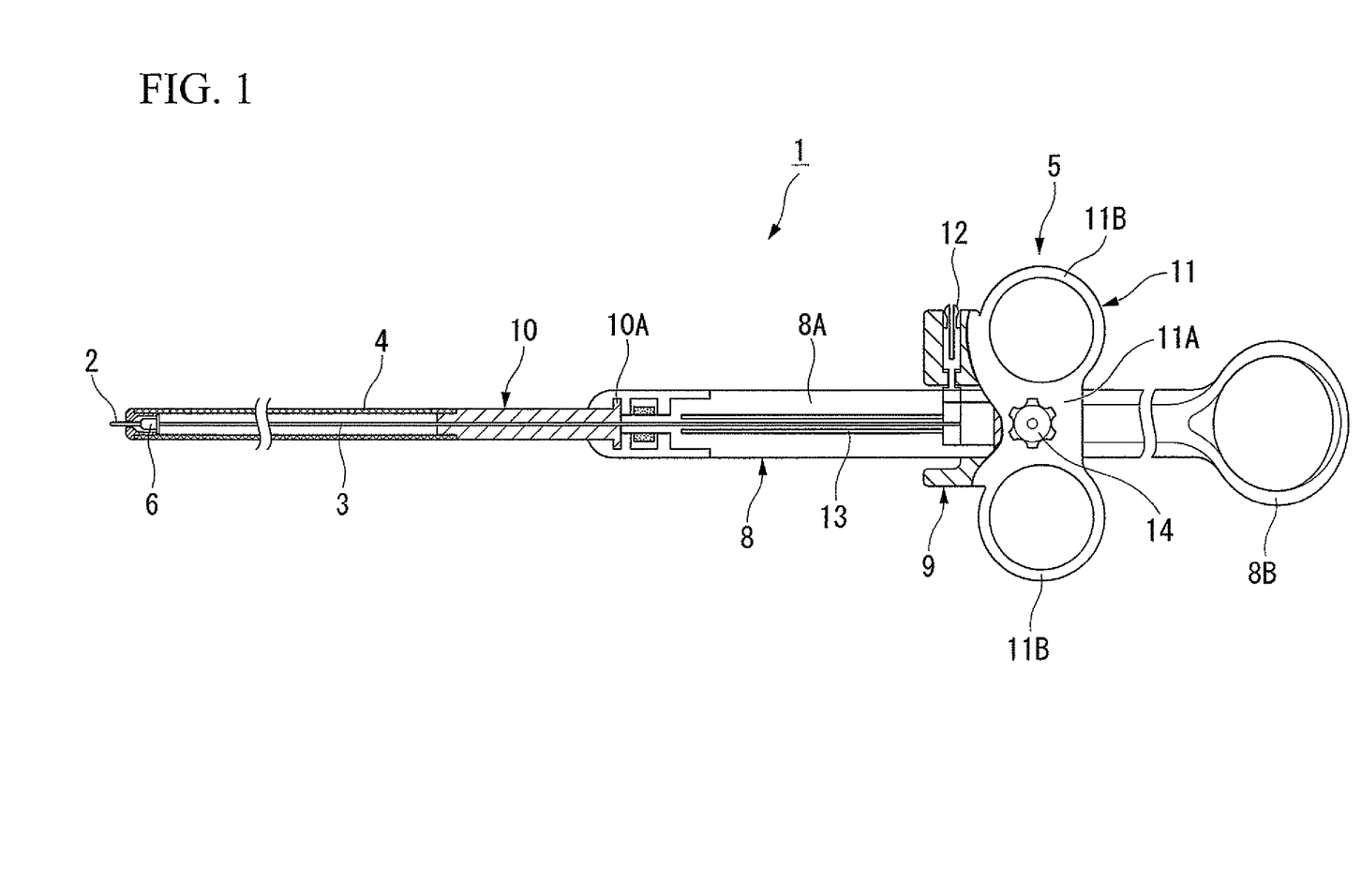
FIG. 1 is a cross-sectional view showing an endoscopic instrument according to a first embodiment of the present invention.

FIG. 1 is a cross-sectional view showing an instrument 1 of the present embodiment. The instrument 1 includes a wire 3 having a high-frequency knife (incising section) 2 attached to the distal end thereof; a sheath 4 that covers the outer periphery of the wire 3; and a maneuvering section 5 for maneuvering the wire 3 and the sheath 4.

The high-frequency knife (simply hereinafter called knife) 2 made of a metal bar having a length of 3 mm etc. is subject to high-frequency power supply to carry out incisional intervention for coelomic tissue as explained later. The knife 2 may be a pad shape or a hook shape in place of a bar shape.

Figure 2:
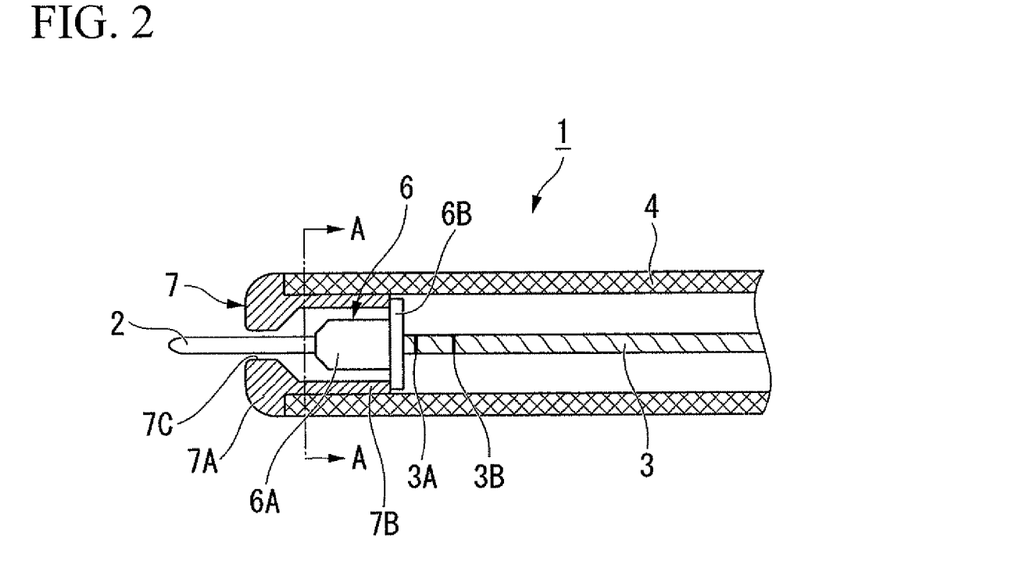
FIG. 2 is an enlarged view showing the vicinity of the distal end of the endoscopic instrument.

FIG. 2 is an enlarged view of the vicinity of the distal end of the instrument 1. The wire 3 made of metal having superior torque transmissibility, e.g., stainless steel is inserted through the inner sheath 4 which will be explained later. Provided between the distal end of the wire 3 and the proximal end of the knife 2 is a stopper 6 projecting outward radially relative to the knife 2. The stopper 6 may be provided to the wire 3 or the knife 2. Two marks 3A and 3B provided at an interval of e.g., 1 millimeter in the vicinity of the distal end of the wire 3 can be recognized visually from the outside of the sheath 4.

The sheath 4 is a transparent tubular member made of insulative and elastic resin etc. A distal end member 7 is fixed to the distal end of the sheath 4 by a press-fitting method. The insulative distal end member 7 made of resin, or rubber, etc. includes a disk section (second-distal-regulation section) 7A disposed outside of the sheath 4; and a cylinder section (first-distal-regulation section) 73 fixed in the sheath 4. Formed in the center of the disk section 7A is a through-hole 7C which allows the knife 2 to pass therethrough.

Figure 3A:
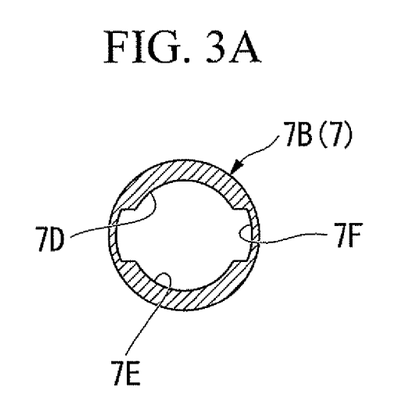
FIG. 3A is a cross-sectional view of the distal end member taken along a line A-A of FIG. 2.
Figure 3B:
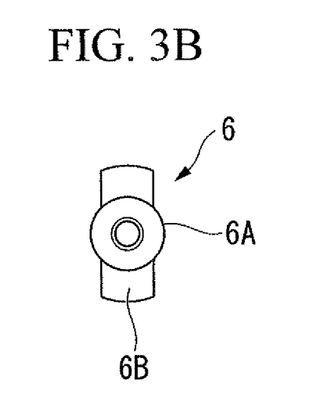
FIG. 3B shows a stopper viewed from the distal end of a sheath.
Figure 4:
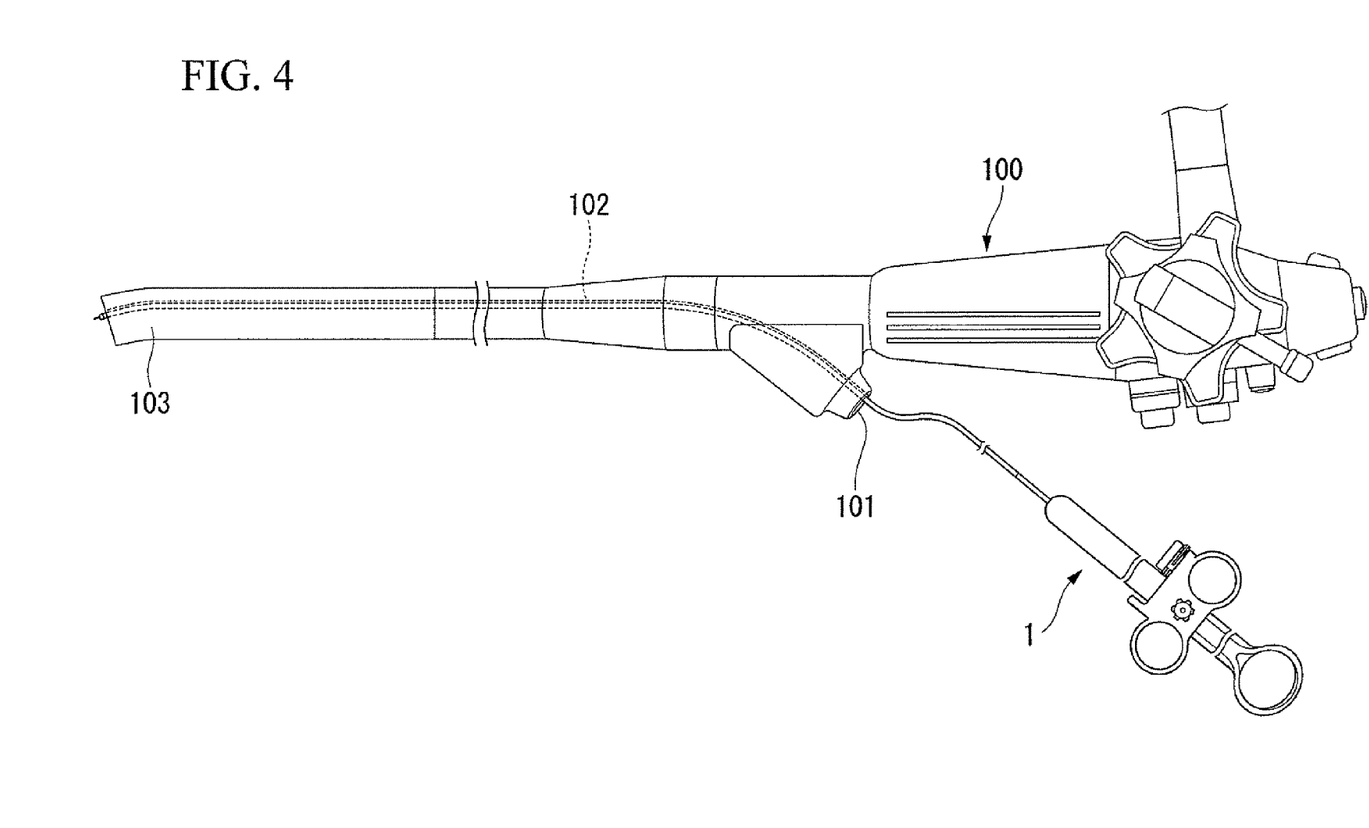
FIG. 4 is a general view showing the endoscopic instrument inserted through an endoscope.

FIG. 3A is a cross-sectional view of the cylinder section 7B taken along a line A-A of FIG. 2. FIG. 3B shows the stopper 6 viewed from the distal end of the sheath 4. The stopper 6 includes a cylindrical central section 6A having a through-hole which allows the knife 2 to pass therethrough; and a flange section (engagement section) 63 projecting outward radially relative to the central section 6A.

The cylinder section 7B has a substantial-rectangular projection-length-adjusting hole 7D provided thereon. The projection-length-adjusting hole 7D has a central section 7E having a substantial round cross-section; and a periphery section (mating engagement section) 7F projecting outward radially relative to the central section 7E. The inner diameter of the central section 7E is set to be greater than the outer diameter of the central section 6A of the stopper 6. This configuration allows the central section 6A to make distal and proximal sliding movement in the central section 7E, and the flange section 6B to make distal and proximal sliding movement in the periphery section 7F.

FIG. 1 shows the configuration of the maneuvering section 5 provided with a main body 8 having the sheath 4 fixed thereto; and a slider 9 having the wire 3 fixed thereto.

The bar-shaped main body 8 has a guide groove 8A extending in an axial direction thereof that allows the slider 9 to make sliding movement. Fixed to the distal end of the main body 8 is a tubular rotor 10 which is capable of freely rotating around the axial line relative to the main body 8 and has a disk-shaped engagement section 10A. The proximal end of the sheath 4 is fixed to the distal end of the rotor 10. That is, the sheath 4 fixed to the rotor 10 is freely rotative relative to the main body 8. Provided to the proximal end of the main body 8 is a finger hook ring 8B for operation.

The slider 9 includes a maneuvering member 11 which has a cylindrical section 11A surrounding the outer periphery of the main body 8 and a finger hook handle 11B for operation; and a plug 12 attached to the maneuvering member 11 and connected to a high-frequency power supply, not shown in the drawing. The proximal end of the wire 3 inserted through the rotor 10 is inserted through a buckling-preventive pipe 13 made of rigid material. The proximal end of the wire 3 and the proximal end of the buckling-preventive pipe 13 are connected and fixed to the plug 12 in the guide groove 8A by fixing means, e.g., screws not shown in the drawing. That is, the first slider 9 and the wire 3 are attached to the main body 8 and are capable of freely sliding in an axial direction along the guide groove 8A.

In addition, the maneuvering member 11 has a fixture dial 14 for fixing the maneuvering member 11 at an arbitrary position on the main body 8. The maneuvering member 11 may be fixed to the main body 8 by forming a pair of engageable shapes at arbitrary positions of the main body 8 and the maneuvering member 11 in place of the fixture dial 14.

Operations in using the instrument 1 having the aforementioned configuration will be explained as follows.

In the beginning, the insertion section of an endoscope is inserted into body cavity of a patient, etc., and the distal end of the insertion section is moved to the vicinity of object tissue for intervention.

Full proximal retraction of the slider 9 of the instrument 1 causes the knife 2 into the sheath 4. The distal end of the sheath 4 is inserted from a forceps port 101 opening on a maneuvering section of the endoscope 100 into an operation channel 102 illustrated in FIG. 4, and then the distal end of the instrument 1 is projected from the distal end of an insertion section 103. Subsequently, an electric power cord, not shown in the drawing, is connected to the plug 12. The electric power cord may be connected prior to insertion of the instrument 1 into the endoscope 100.

Pushing this state of slider 9 and extending the wire 3 until abutting the stopper 6 to the distal end member 7 cause the knife 2 to project from the distal end of the sheath 4. Maneuvering of the sheath 4 or the main body 8 enables two different stepwise adjustments to the projection length of the knife 2.

FIG. 2 shows a first formation in which the flange section 6B of the stopper 6 makes contact with the proximal end of the cylinder section 7B of the distal end member 7. The cylinder section 7B in the first formation regulates distal sliding movement of the wire 3. The present embodiment sets this state of the knife 2 to maintain 1.5 millimeter of projection length.

Figure 5A:
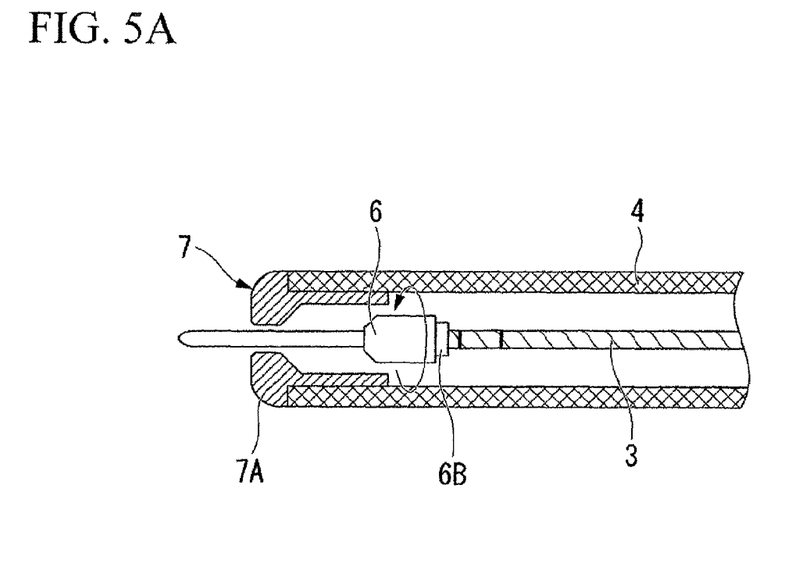
FIGS. 5A and 5B show movement of the vicinity of the distal end of the endoscopic instrument in use.

Rotating the main body 8 in the first formation around the axial line relative to the sheath 4 while in relation to the rotor 10 or the sheath 4 causes the slider 9 to rotate together with the main body 8, thereby moving the wire 3 and the stopper 6 rotatively relative to the distal end member 7 as illustrated in FIG. 5A.

Figure 5B:
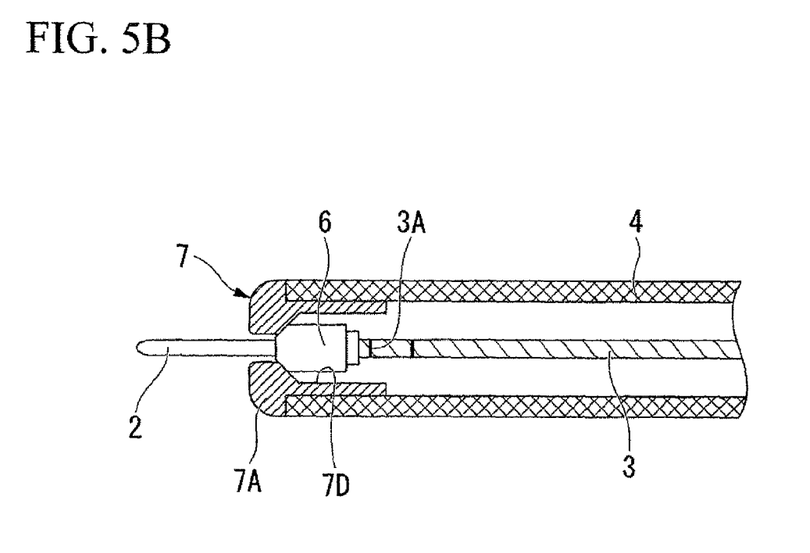

Maneuvering like this in an attempt to coincide the position of the flange section 6B of the stopper 6 with the position of the periphery section 7F of the projection-length-adjusting hole 7D of the distal end member 7 provides a predetermined rotational angle of relative rotation to the main body 8. The flange section 6B engaging with the periphery section 7F accordingly allows the stopper 6 to enter the projection-length-adjusting hole 7D. Moving the slider 9 distally causes the stopper 6 to make distal movement in the projection-length-adjusting hole 7D and make contact with the disk section 7A of the distal end member 7. This is a second formation as shown in FIG. 5B.

The disk section 7A in the second formation regulates distal sliding movement of the wire 3. The present embodiment sets this state of the knife 2 to maintain e.g., 2.0 millimeter of projection length which is longer than that of the first formation.

A mark 3A, which is the most distal mark provided to the wire 3 in the distal end member 7 of the second formation, cannot be visually recognized from the outside of the sheath 4.

Upon obtaining a desirably adjusted projection length of knife 2 in the aforementioned operations, the slider 9 is fixed to the main body 8 by using the fixture dial 14 if necessary. Subsequently, high-frequency electric current is applied to the knife 2 to carry out incisional or dissectional intervention to object tissue.

In the present embodiment, providing a predetermined angle of rotation to the main body 8 relative to the sheath 4 of the instrument 1 causes the flange section 6B of the stopper to engage with the periphery section 7F of the projection-length-adjusting hole 7D. This results in allowing a portion where the stopper 6 makes contact with the distal end member 7 to move from the proximal end of the cylinder section 7B to the disk section 7A, thereby adjusting and maintaining two different stepwise projection lengths of the knife 2 from the sheath 4 easily and reliably. Therefore, intervention corresponding to the shape of object tissue can be desirably conducted by adjusting the projection length of the knife 2.

In addition, a user can recognize as to which formation the knife 2 is disposed in based on, for example, number of visible marks or positions of the marks relative to the distal end member 7 since the marks 3A and 3B provided to the wire 3 can be recognized from the outside of the sheath 4.

Figure 6:
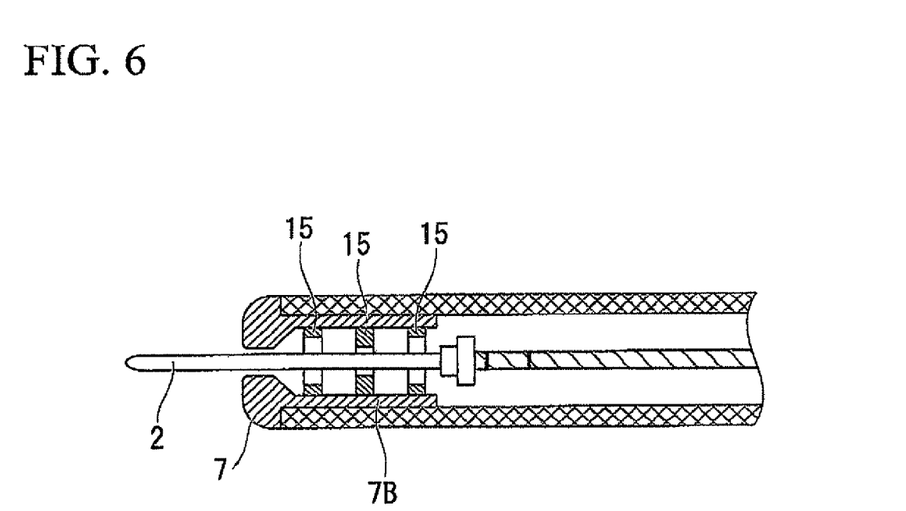
FIG. 6 is an enlarged view showing the vicinity of the distal end of a modified example of the endoscopic instrument.

The present embodiment previously explained with reference to the example regulating distal sliding movement of the wire 3 at two points, i.e., the proximal end of the cylinder section 7B and the disk section 7A may be replaced by a modified example of the configuration shown in FIG. 6 in which two or more distal-regulation section members 15 each having a projection-length-adjusting hole having the same shape as that of the projection-length-adjusting hole 7D are disposed in the cylinder section 7B so that the positions of the adjacent distal-regulation section members 15 are different from each other in a circumferential direction of the periphery portion to regulate distal sliding movement of the wire 3 at three or more positions. Accordingly, the knife 2 can maintain more increased stepwise projection length.

Also, the present embodiment previously explained with reference to the example which rotates the main body 8 while the sheath 4 is fixed may be replaced by a configuration which rotates the sheath 4 relative to the main body 8 by rotating the sheath 4 while the main body 8 is fixed.

In addition, number and interval of marks provided to the wire, previously explained for example but not limited to the aforementioned embodiments, may be determined optionally. In addition, marks externally visible from the sheath 4 may be provided to the stopper 6 and the distal end member 7 to facilitate coinciding the flange section 6B to the periphery section 7F of the projection-length-adjusting hole 7D in position while the stopper 6 moves relative to the sheath 4.

An instrument according to a second embodiment of the present invention will be explained next with reference to FIGS. 7 and 8.

The difference of an instrument 21 according to the present embodiment from the endoscopic instrument 1 of the aforementioned first embodiment is based on a fact that a distal end member and a stopper have engageable female and male screw threads formed thereon.

Note that components that are in common with those of the aforementioned instrument 1 will be assigned the same numeric symbol and redundant explanation thereof will be omitted.

Figure 7:
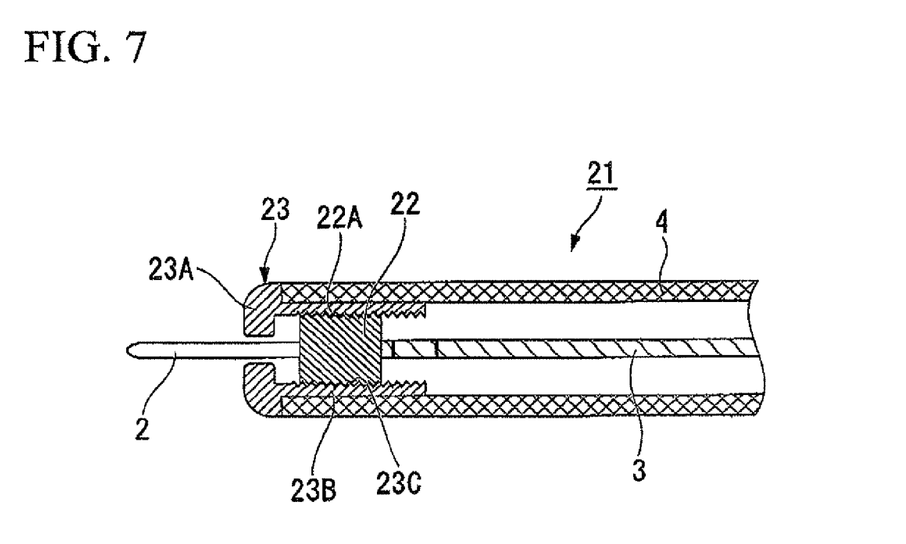
FIG. 7 is an enlarged view showing the vicinity of the distal end of an endoscopic instrument according to a second embodiment of the present invention.
Figure 8:
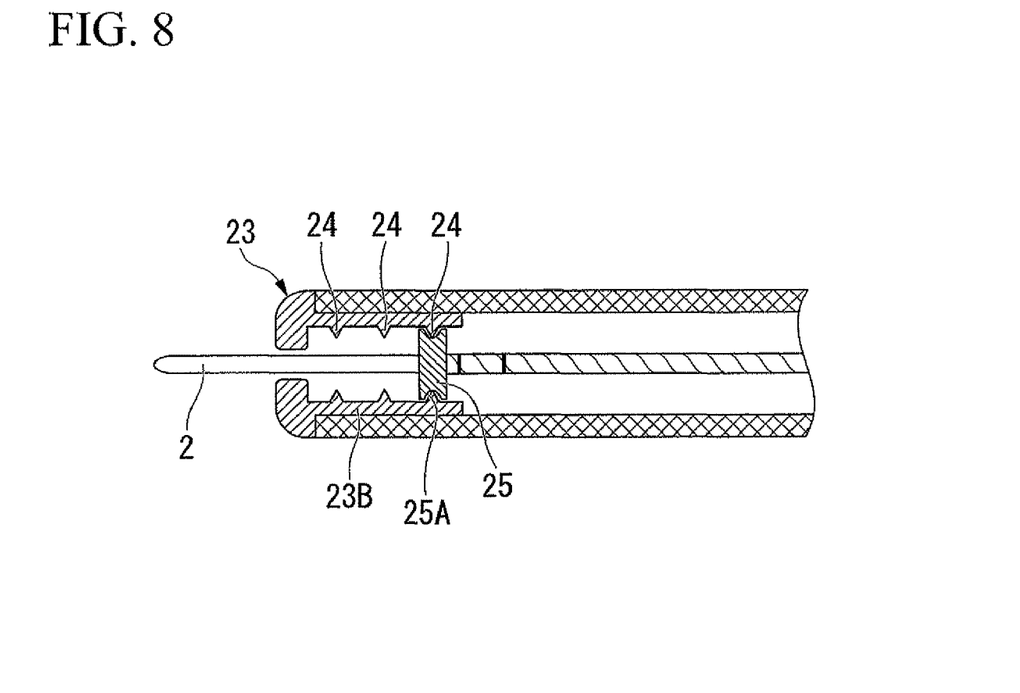
FIG. 8 is an enlarged view showing the vicinity of the distal end of a modified example of the endoscopic instrument.

FIG. 7 is an enlarged view of the vicinity of the distal end of the instrument 21. A stopper 22 of the instrument 21 free from a flange section is a cylinder substantially. A distal end member (screwing member) 23 has a disk section 23A and a cylindrical section 23B similarly to the distal end member 7 of the first embodiment. The cylindrical section 23B is provided with a screw groove 21C formed on the inner periphery surface thereof in place of a projection-length-adjusting hole. Provided on the outer periphery of the stopper 22 is a male thread 22A which is engageable with the screw groove 23C. A screw groove may be formed in either one of the components, and also, a screw thread may be formed to either one of the components as long as the screw thread can engage with the screw thread.

Operations in using the instrument 21 having the aforementioned configuration will be explained.

In the beginning, an endoscope is inserted into a patient's body by the same method as that of the first embodiment to project the distal end of the instrument 1 from the distal end of the instrument 1.

Rotating the sheath 4 relative to the main body 8 by the same method as that of the first embodiment causes the male thread 22A of the stopper 22 to engage with the female screw 23C of the distal end member 23, thereby allowing the stopper 22 to make distal and proximal movement in the cylindrical section 23B. Changing screw-engaging length between the stopper 22 and the distal end member 23 by adjusting rotation amount (rotational angle) of the sheath 4 relative to the main body 8 provides stepless adjustment to the projection length of the knife 2. Engagement between the male thread 22A and the female screw 23C preventing sliding movement of the slider 9 allows the knife 2 to maintain a desirable projection length.

Rotation of the sheath 4 relative to the main body 8 of the instrument 21 according to the present embodiment provides distal or proximal gradual movement to the stopper 22 in the cylindrical section 23B of the distal end member 23. Therefore, adjusting the engagement length between the stopper 22 and the distal end member 23 provides fine adjustment to the projection length of the knife 2.

Also, the wire 3 can make a sliding movement only by rotating the sheath 4 relative to the main body 8 because the male thread 22A engages with the female screw 23C. Therefore, distal and proximal movements of the knife 2 caused by wobbling etc. of the slider 9 are eliminated; thus, stable intervention can be carried out.

The present embodiment previously explained with reference to the example providing a screw groove formed on the substantially all the inner surface of the cylindrical section 23B may be replaced by a modified example of configuration shown in FIG. 8 providing: a plurality of screw threads (first-distal-regulation section) 24 at a predetermined interval so that each screw thread has a circumferential length corresponding to an inner periphery of the cylindrical section 23B; and the corresponding number of screw grooves 25A having the substantial same length of the screw thread 24 on the outer periphery of a stopper 25. An instrument based on this configuration can maintain a plurality of stepwise adjusted projection lengths of the knife 2 by relatively small rotational operation since the stopper 25 can slide freely in sections free from the screw threads 24.

Preferably, the length of the stopper 25 in the sliding direction should be set shorter than the interval between the screw threads 24 because shorter length of stopper 25 permits an operator to recognize an engaging section and a non-engaging section between the screw threads 24 and the stopper 25. Elongated continuous stopper 25 prevents from the operator to conduct stepwise adjustment of the knife.

An instrument according to a third embodiment of the present invention will be explained next with reference to FIGS. 9 and 10. Difference of an instrument 31 according to the present embodiment from the aforementioned endoscopic instrument 1 is based on the shape of a distal end member and shape of a stopper.

Note that components that are in common with those of the aforementioned instrument 1 will be assigned the same numeric symbol and redundant explanations thereof will be omitted.

Figure 9:
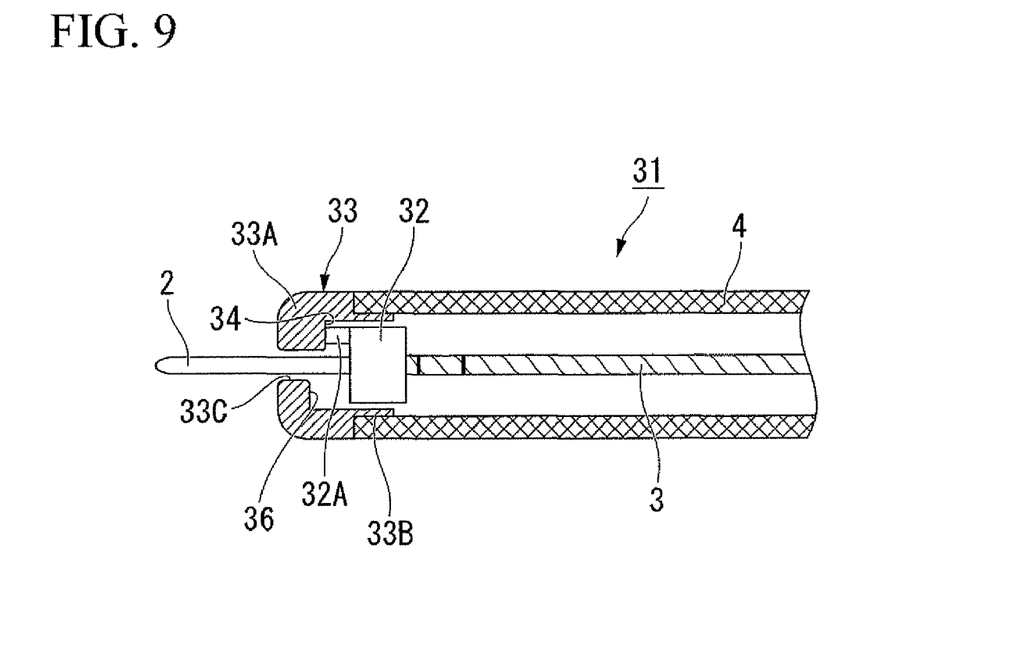
FIG. 9 is an enlarged view showing the vicinity of the distal end of an endoscopic instrument according to a third embodiment of the present invention.

FIG. 9 is an enlarged view of the vicinity of the distal end of the instrument 31. Provided to a stopper 32 of the instrument 31 is a distally projecting abutment section 32A. Provided to the proximal end of a disk section 33A of a distal end member 33 are three abutment surfaces making contact with the abutment section 32A to regulate distal sliding movement of the wire 3.

Figure 10:
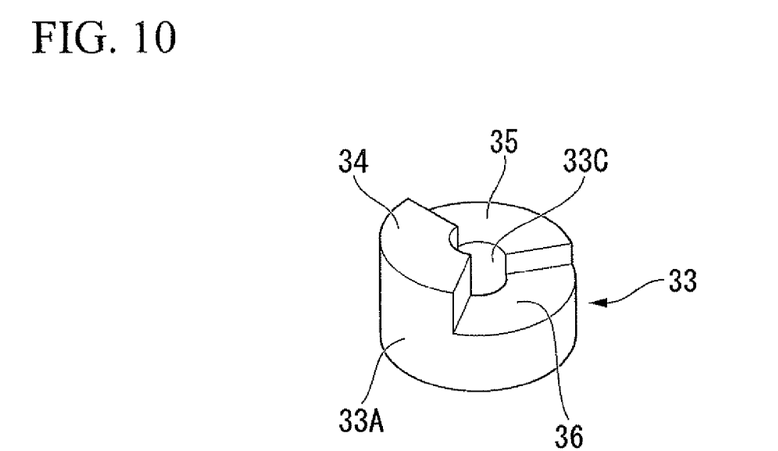
FIG. 10 is a schematic view showing the distal end member of the endoscopic instrument.

FIG. 10 is a schematic view showing the shape of the disk section 33A of the distal end member 33. Note that, a cylinder section 33B that is press-fit into the sheath 4 is omitted in the drawing to help better showing the shape of the disk section 33A. Provided to the proximal ends of the disk section 33A are three substantial-fan-shaped abutment surfaces, i.e., a first abutment surface 34, a second abutment surface 35, and a third abutment surface 36 provided separately in the circumferential direction around a through-hole 33C which allows the knife 2 to be inserted therethrough. Each abutment surface is not limited to having a fan-shape, and each area may be different.

Distance, hereinafter called thickness, of each abutment surface from the distal end (bottom surface in FIG. 10) of the disk section 33A is different by e.g., 0.5 millimeter among the abutment surfaces. The proximal end of the disk section 33A in general is formed to have substantial spiral staircases.

Operations using the instrument 31 having the aforementioned configuration will be explained as follows.

In the beginning, the distal end of the instrument 31 is projected from the distal end of the insertion section 103 of the endoscope 100 by the same method as that of the first embodiment.

Maneuvering the slider 9 causes the wire 3 to extend and the abutment section 32A of the stopper 32 to make contact with one of the following: first abutment surface 34, the second abutment surface 35, and the third abutment surface 36; thereby regulating distal sliding movement of the wire 3. The instrument 31 is set to maintain the shortest, e.g., 1.0 millimeter of projection length of the knife 2 while the abutment section 32A abuts the first abutment surface 34 as illustrated in FIG. 9.

Rotating the sheath 4 relative to the main body 8 by the same operation as that of the first embodiment causes the stopper 32 relative to the distal end, thereby changing correlation between the abutment section 32A and each abutment surfaces 34, 35, and 36. Maneuvering in this way, i.e., changing distal abutment surfaces of the abutment section 32A repeatedly causes the knife 2 to make distal or proximal movement and changes the projection length according to the difference of thickness of the second maneuvering member 18 making contact with the abutment section 32A.

The distal section of the instrument 31 according to the present embodiment can obtain simple configuration having relatively fewer number of components.

Also, maneuvering, i.e., rotation of the 4 free from causing the 155 to making contact with the distal end member 33 facilitates transmitting rotation of the sheath 4 relative to the main body 8 to the wire 3. Therefore, relatively small rotational operation can rotate the wire 3 and the stopper 32.

An instrument according to a fourth embodiment of the present invention will be explained next with reference to FIGS. 11 and 12. Differences between an instrument 41 according to the present embodiment from the aforementioned endoscopic instrument 1 is based on shape of a distal end member and shape of a stopper.

Note that components that are in common with those of the aforementioned instrument 1 will be assigned the same numeric symbol and redundant explanations thereof will be omitted.

Figure 11:
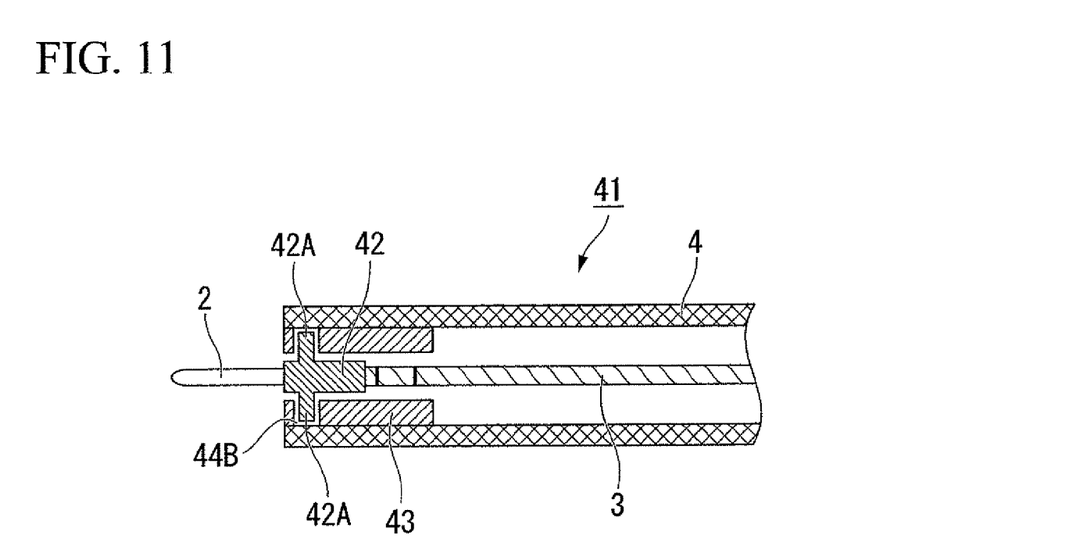
FIG. 11 is an enlarged view showing the vicinity of the distal end of the endoscopic instrument according to the third embodiment of the present invention.

FIG. 11 is an enlarged view showing the vicinity of the distal end of the instrument 41. Provided to a stopper 42 of the instrument 41 is a pair of flange sections (engagement projection sections) 42A projecting radially outward. The flange sections 42A, not limited to specific shape, may have round shape since it is preferable to facilitate maneuvering, i.e., adjusting the projection length of the knife 2, which will be explained later.

A substantial cylindrical distal end member 43 has, on the inner periphery thereof, two pairs of fixture grooves making contact with the stopper and cam grooves joining the fixture grooves.

Figure 12:
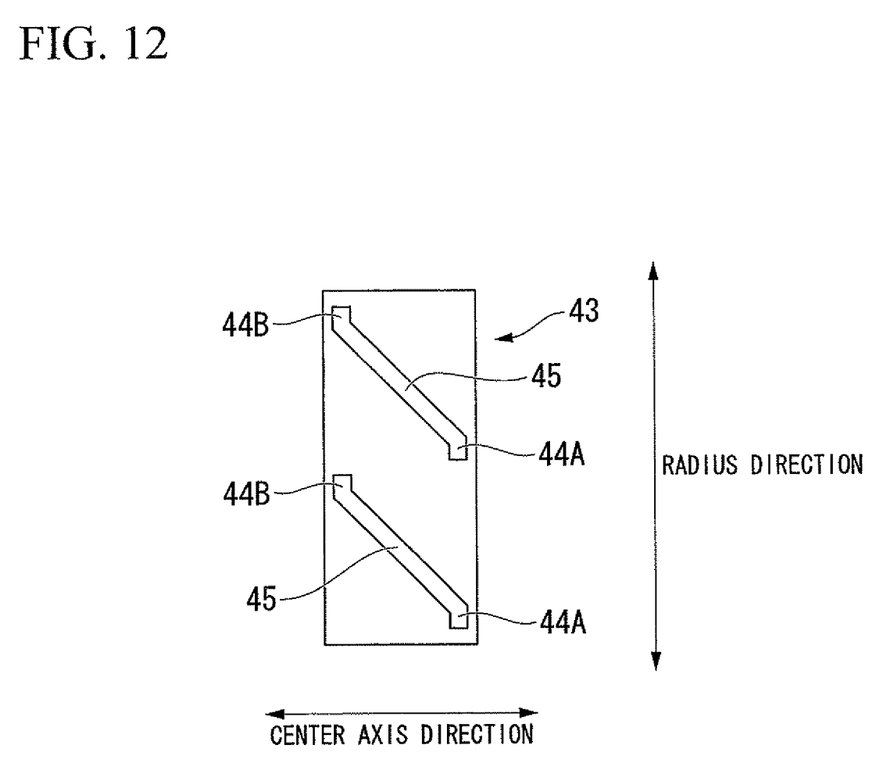
FIG. 12 is a developed view showing the inner periphery of the distal end member of the endoscopic instrument.

FIG. 12 is a developed view showing the inner periphery of the distal end member 43. A distal fixture groove (engagement groove) 44A is joined to a distal fixture groove 44B by the two cam grooves 45 disposed in parallel. Each flange section 42A of the stopper 42 engages with the fixture groove 44A.

Operations using an instrument 41 having the aforementioned configuration will be explained as follows.

The knife 2 is set to maintain for example, 1.0 millimeter of projection length while the flange section 42A of the stopper 42 making contact with the fixture groove 44A regulates distal sliding movement of the wire 3.

Rotating the sheath 4 relative to the main body 8 maneuvered by the same method as that of the first embodiment causes the stopper 42 to rotate. The rotation of the stopper 42 causes the flange sections 42A to make distal movement on the cam grooves 45, thereby causing the stopper 42 and the wire 3 to make distal sliding movement in the distal end member 43 until reaching the fixture groove 44B.

The flange section 42A upon reaching and abutting the fixture groove 44B as illustrated in FIG. 11 regulates distal sliding movement of the wire 3, thereby fixing the knife 2. This state of the knife 2 is set to maintain for example, 2.0 millimeter of projection length. Consequently, the instrument 41 subject to the aforementioned operation is set to adjust projection length of the knife 2 and maintain thereof at two different steps.

The instrument 41 according to the present embodiment having the flange section 42A previously engaging with the fixture grooves and the cam grooves is free from positioning of the flange section relative to the engagement section for sliding the stopper distally toward the fixture grooves 44B. Therefore, the instrument may have a configuration which can facilitate adjustment of the projection length of the knife 2.

In addition, the instrument may have a configuration which can adjust the projection length since relatively small rotation of the stopper, for example, approximately a maximum 360 degrees of rotation can slide the flange section 42A to the fixture groove 44B.

The technical scope of the present invention is not limited to the embodiments described above. Rather, various modifications may be added without deviating from the spirit of the invention.

For example, a usable wire in the aforementioned embodiments may be a multi-thread coil or a multi-thread-and-multi-layer coil. Improved torque transmissibility of the wire 3 in this configuration facilitates maneuvering of relative rotational movement for adjusting the projection length of a knife.

Alternatively, the aforementioned embodiment, explained with reference to the example in which the stopper abuts the first and second-distal-regulation sections in the vicinity of the distal end of the sheath, may be replaced by a configuration in which the stopper abuts the first-distal-regulation member farther distally to regulate distal sliding movement of the wire. However, a mid point of the outer sheath in many cases is bending because an instrument for use is inserted through an endoscope. Therefore, preferably, the stopper should abut the vicinity of the hardly bending distal end of the outer sheath to provide desirable projection length control.

What is claimed is:

1. An endoscopic instrument comprising:
   an incising section inserted into a body cavity endoscopically for incisional intervention;
   a wire having a distal end connected to the incising section;
   a sheath, made from insulative material, for allowing the wire to pass therethrough;
   a main body having a proximal end of the sheath fixed thereto, the proximal end being capable of freely rotating in a circumferential direction;
   a slider, having a proximal end of the wire fixed thereto, disposed slidably in an axial line direction of the main body;
   a stopper, provided to the incising section or the wire, for projecting outward radially relative to the wire;
   a first-distal-regulation section, provided to the sheath, for regulating distal sliding movement of the wire by making contact with the stopper; and
   a second-distal-regulation section, provided distally relative to the first-distal-regulation section, for regulating distal sliding movement of the wire by making contact with the stopper, wherein
   the stopper is capable of moving between the first-distal-regulation section and the second-distal-regulation section by rotating the main body relative to the sheath around an axial line by a predetermined rotational angle, and
   the incising section can be maintained at two different projection lengths based on the stopper making contact with the first-distal-regulation section or the stopper making contact with the second-distal-regulation section.

2. The endoscopic instrument according to claim 1, wherein the stopper is capable of moving between the first-distal-regulation section and the second-distal-regulation section by engaging mating engagement sections provided to the stopper and to the first-distal-regulation section and by rotating the main body relative to the sheath around the axial line by the predetermined rotational angle.

3. The endoscopic instrument according to claim 1, wherein a screw groove is formed to one of the stopper and the first-distal-regulation section, and a screw thread engaging with the screw groove is formed to the other.

4. The endoscopic instrument according to claim 1, wherein
   the first-distal-regulation section and the second-distal-regulation section are engagement grooves, formed on an inner periphery of the sheath, the first-distal-regulation section and the second-distal-regulation section being connected by cam grooves provided on the inner periphery of the sheath,
   the stopper has engagement projection sections engaging with the engagement grooves, and
   the stopper upon moving the engagement projection sections on the cam grooves moves between the first-distal-regulation section and the second-distal-regulation section.

5. The endoscopic instrument according to claim 1, wherein the first-distal-regulation section and the second-distal-regulation section are a first abutment surface and a second abutment surface provided proximally relative to a projection-length-adjusting member fixed to the sheath, and the first abutment surface and the second abutment surface are disposed at different positions in circumferential directions with respect to the projection-length-adjusting member.

6. The endoscopic instrument according to one of claims 1 to 5, wherein the wire is a multi-thread coil or a multi-thread-and-multi-layer coil.

* * * * *